(12) United States Patent
Rojo et al.

(10) Patent No.: US 10,908,000 B2
(45) Date of Patent: Feb. 2, 2021

(54) ANTIFOULING ACCESSORY FOR FIELD DEPLOYED SENSORS AND INSTRUMENTS

(71) Applicant: YSI, INC., Yellow Springs, OH (US)

(72) Inventors: Miguel Angel Rojo, West Carrollton, OH (US); Tiffany Lavon Schirmer, Waynesville, OH (US)

(73) Assignee: YSI, INC., Yellow Springs, OH (US)

( * ) Notice: Subject to any disclaimer, the term of this patent is extended or adjusted under 35 U.S.C. 154(b) by 0 days.

(21) Appl. No.: 16/030,008

(22) Filed: Jul. 9, 2018

(65) Prior Publication Data

US 2019/0063965 A1    Feb. 28, 2019

Related U.S. Application Data

(60) Provisional application No. 62/529,594, filed on Jul. 7, 2017.

(51) Int. Cl.
| | |
|---|---|
| *G01C 13/00* | (2006.01) |
| *G01D 11/24* | (2006.01) |
| *H05K 5/03* | (2006.01) |
| *B08B 17/04* | (2006.01) |
| *G01N 33/18* | (2006.01) |

(52) U.S. Cl.
CPC .......... *G01D 11/245* (2013.01); *B08B 17/04* (2013.01); *G01C 13/00* (2013.01); *H05K 5/03* (2013.01); *G01N 33/18* (2013.01)

(58) Field of Classification Search
CPC .............. G01D 11/24; G01D 11/245
See application file for complete search history.

(56) References Cited

U.S. PATENT DOCUMENTS

| | | | | |
|---|---|---|---|---|
| 3,867,630 A | * | 2/1975 | Urban | B63B 59/04 |
| | | | | 250/239 |
| 5,321,268 A | * | 6/1994 | Crosby | G01J 1/58 |
| | | | | 250/361 R |
| 5,633,460 A | * | 5/1997 | Manmaru | B08B 17/00 |
| | | | | 73/170.29 |
| 6,303,078 B1 | * | 10/2001 | Shimizu | D06M 16/00 |
| | | | | 422/8 |
| 7,341,695 B1 | * | 3/2008 | Garner | B08B 17/06 |
| | | | | 422/500 |
| 8,429,952 B1 | * | 4/2013 | Bringhurst | A01N 59/16 |
| | | | | 73/53.01 |

(Continued)

OTHER PUBLICATIONS

Navarro-Villoslada, F., et al., "Fiber-optic luminescent sensors with composite oxygen-sensitive layers and anti-biofouling coatings," Analytical chemistry vol. 73.21, 2001, pp. 5150-5156.

(Continued)

*Primary Examiner* — Jamel E Williams
(74) *Attorney, Agent, or Firm* — Ware, Fressola, Maguire & Barber LLP

(57) ABSTRACT

A sensor device for deploying in an environmental field having macroorganisms and for performing environmental monitoring, features a sensor body and an antifouling device or guard. The sensor body includes at least one instrument or sensor configured to sense to one or more environmental conditions in the environmental field and provide signaling containing information about the one or more environmental conditions sensed. The antifouling device or guard couples to the sensor body, covers part of the at least one instrument or sensor, and protects a covered part of the at least one instrument or sensor from the macroorganisms.

21 Claims, 6 Drawing Sheets

(56) References Cited

U.S. PATENT DOCUMENTS

| | | | | |
|---|---|---|---|---|
| 8,514,664 | B2* | 8/2013 | Harrick | G01V 3/15 |
| | | | | 181/120 |
| 8,644,109 | B2* | 2/2014 | Vignaux | G01V 1/201 |
| | | | | 367/20 |
| 8,998,535 | B2* | 4/2015 | Stenzel | B63B 22/22 |
| | | | | 405/171 |
| 9,116,253 | B2* | 8/2015 | Stenzel | A01N 59/16 |
| 9,250,342 | B2* | 2/2016 | Vignaux | G01V 1/201 |
| 9,465,127 | B2* | 10/2016 | Karlsen | G01V 13/00 |
| 9,562,163 | B2* | 2/2017 | Lobe | A01N 55/00 |
| 9,709,689 | B2* | 7/2017 | Harrick | G01V 13/00 |
| 2011/0169630 | A1* | 7/2011 | Nolfi | F01D 17/02 |
| | | | | 340/539.1 |
| 2011/0174207 | A1* | 7/2011 | Harrick | C09D 5/1618 |
| | | | | 114/244 |
| 2012/0176858 | A1* | 7/2012 | Stenzel | A01N 59/16 |
| | | | | 367/20 |
| 2013/0039153 | A1* | 2/2013 | Hartshorne | B63B 59/04 |
| | | | | 367/153 |
| 2013/0337201 | A1* | 12/2013 | Eyster | A61B 90/39 |
| | | | | 428/35.5 |
| 2014/0041450 | A1* | 2/2014 | MacQuin | G01V 1/3843 |
| | | | | 73/431 |
| 2014/0151308 | A1* | 6/2014 | Kelly | C02F 1/50 |
| | | | | 210/739 |
| 2014/0247690 | A1* | 9/2014 | MacQuin | G01V 1/3843 |
| | | | | 367/15 |
| 2015/0253442 | A1* | 9/2015 | Hartshorne | G01V 1/38 |
| | | | | 367/15 |

OTHER PUBLICATIONS

Manov, Derek V., Grace C. Chang, and Tommy D. Dickey, "Methods for reducing biofouling of moored optical sensors," Journal of Atmospheric and Oceanic Technology vol. 21.6, 2004, pp. 958-968.

* cited by examiner

Single sensor/instrument 16 individually surrounded in foam 30 with a heat sink tubing 36 used to hold the foam 30 in place

ANTIFOULING ACCESSORY FOR FIELD DEPLOYED SENSORS AND INSTRUMENTS

CROSS-REFERENCE TO RELATED APPLICATIONS

This application claims benefit to provisional patent application Ser. No. 62/529,594, filed 7 Jul. 2017, which is incorporated by reference in its entirety.

BACKGROUND OF THE INVENTION

1. Field of Invention

This invention relates to a sensor for measuring parameters related to water, e.g., in a river, a stream, a lake, an estuary, a sea, an ocean, etc.

2. Description of Related Art

Biofilms condition the surface of any sensor or instrument, making favorable conditions for macroorganisms, such as barnacles to grow. Minimizing fouling and specifically, biofouling, in environmental monitoring systems is a complicated problem that often limits the deployment length of field sensors or field instruments. Current technology offers sensor protection by use of mechanical wiping, copper laden accessories and/or UV irradiation. The current accessories create a hostile environment for biofouling agents such as barnacles and the like. Tedious sensor deployment preparation involves wrapping sensors/instruments in copper tape and typically only offers one use per deployment. UV irradiation requires external power, which limits deployment site selection due to the power requirements of the system.

In view of this, there is a need in the industry for a better way for minimizing fouling and specifically, biofouling, in environmental monitoring systems

SUMMARY OF THE INVENTION

The present invention provides a reusable antifouling accessory for protecting field sensors or instruments to control fouling build-up. By way of example, the antifouling accessory may be installed around the outside of the one or more sensors or instruments, minimizing available sensor/instrument surface area for fouling. Minimizing the available surface area for the films to adhere, greatly decreases the amount of biological growth which translates into decreased time spent cleaning post deployment.

According to the present invention, one or more antifouling accessories may include the following materials:
Polymer/plastic;
Copper;
Brass alloy;
Foam;
A combination of plastic and copper, e.g., including:
Plastic with an outer layer of copper,
Copper impregnated plastic, and
Plastic with a copper piece near the sensing area or critical part of the instrument;
A combination of foam and copper, e.g., including:
Foam with an outer layer of copper,
Copper impregnated foam, and
Foam with a copper piece near the sensing area or critical part of the instrument.

By way of example, the antifouling accessories could be secured by the following methods or combination therein:
Zip/cable ties,
Screws,
Epoxy,
Tape,
Press fit,
Interlocking mechanisms,
Heat shrink wrap, and
O-rings.

Specific Embodiments

According to some embodiments, the present invention may include, or take the form of, a sensor device for deploying in an environmental field having macroorganisms and for performing environmental monitoring, featuring a sensor body and an antifouling accessory, e.g., such as an antifouling device or guard.

The sensor body may include at least one instrument or sensor configured to sense to one or more environmental conditions in the environmental field and provide signaling containing information about the one or more environmental conditions sensed.

The antifouling device or guard may be configured to couple to the sensor body, cover part of the at least one instrument or sensor, and protect a cover part of the at least one instrument or sensor from the macroorganisms.

The present invention may include one or more of the following features:

The antifouling device or guard may include an antifouling body having two halves or members that fasten together, e.g., via one set of screws or fasteners. The antifouling device or guard may also include a copper insert, e.g., fastened to the antifouling body via another set of screws.

The two halves or members may be made of plastic, brass alloy, copper, plastic with an outer layer of copper, copper impregnated with plastic, plastic with a copper piece near a sensing area of the instrument or sensor.

The two members may be fastened together with screws, zip cable ties, epoxy, tape, or heat shrink wrap.

The two members may be configured to press fit together.

The sensor device may include a foam barrier configured between the antifouling guard or device and the instrument or sensor.

The foam barrier may include a foam with an outer layer of copper, a copper impregnated foam, a foam with a copper piece near a sensing area of the at least one instrument or sensor.

The foam barrier may include a foam that surrounds the at least one instrument or sensor and a heat shrink tubing to hold the foam in place.

The at least one instrument or sensor may include multiple instruments or sensors; and the foam barrier may include one piece of foam that collectively surrounds the multiple instruments or sensors and a heat shrink tubing to hold the foam in place.

The at least one instrument or sensor may include multiple instruments or sensors; and the foam barrier may include individual pieces of foam that respectively surrounds each of the multiple instruments or sensors and individual heat shrink tubing to hold the individual pieces of foam in place.

Advantages

Advantages of the antifouling accessory according to the present invention, e.g., may include:

Reusability,
Quick installation,
Field changeability,
Inexpensive,
Durability,
Easily arranged to accessorize existing field platforms as well as future field platforms, and
Easily cleaned by conventional methods.

BRIEF DESCRIPTION OF THE DRAWING

The drawing, which are not necessarily drawn to scale, includes FIGS. 1-7, as follows.

Figure 1:
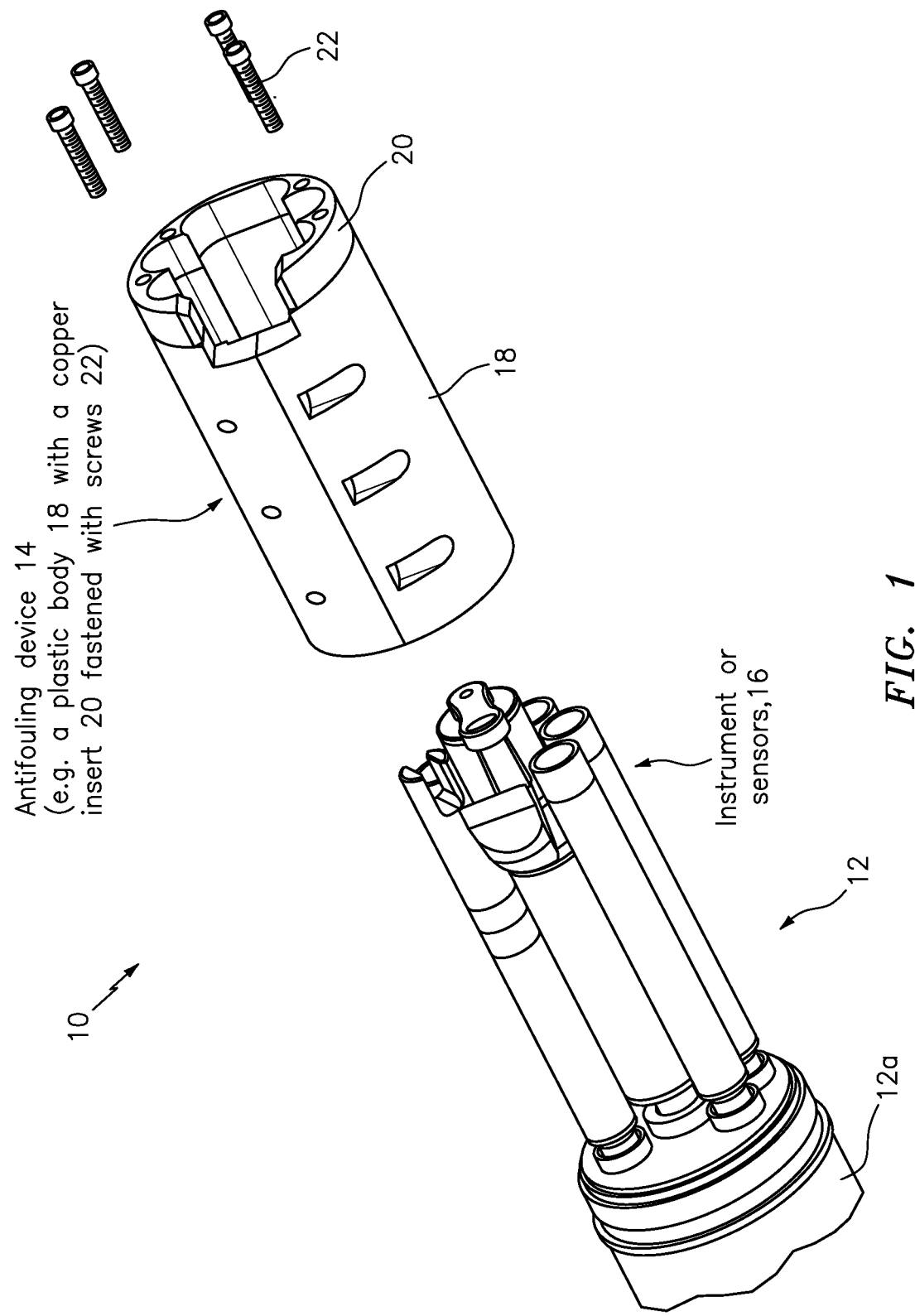
FIG. 1 is an exploded perspective view of a sensor device for deploying in an environmental field having macroorganisms and for performing environmental monitoring, having a sensor body and an antifouling device or guard, where the sensor body includes instruments or sensors, and where the antifouling device or guard takes the form of a plastic antifouling body with a copper insert fastened with screws, according to some embodiments of the present invention.

To reduce clutter in the drawing, each Figure in the drawing does not necessarily include every reference label for every element shown therein.

DETAILED DESCRIPTION OF BEST MODE OF THE INVENTION

FIG. 1

By way of example, FIG. 1 shows a sensor device generally indicated as 10 for deploying in an environmental field having macroorganisms and for performing environmental monitoring of water, e.g., in a river, a stream, a lake, an estuary, a sea, an ocean, etc. The sensor device 10 includes a sensor body generally indicated as 12 and an antifouling accessory, e.g., such as an antifouling device or guard generally indicated as 14. The sensor body 12 includes a sensor body portion 12a and instruments or sensors, one of which is labeled 16. By way of example, the antifouling device or guard 14 may take the form of a plastic antifouling body 18 with a copper insert 20 fastened with screws, one of which is labeled 22.

FIG. 2

Figure 2:
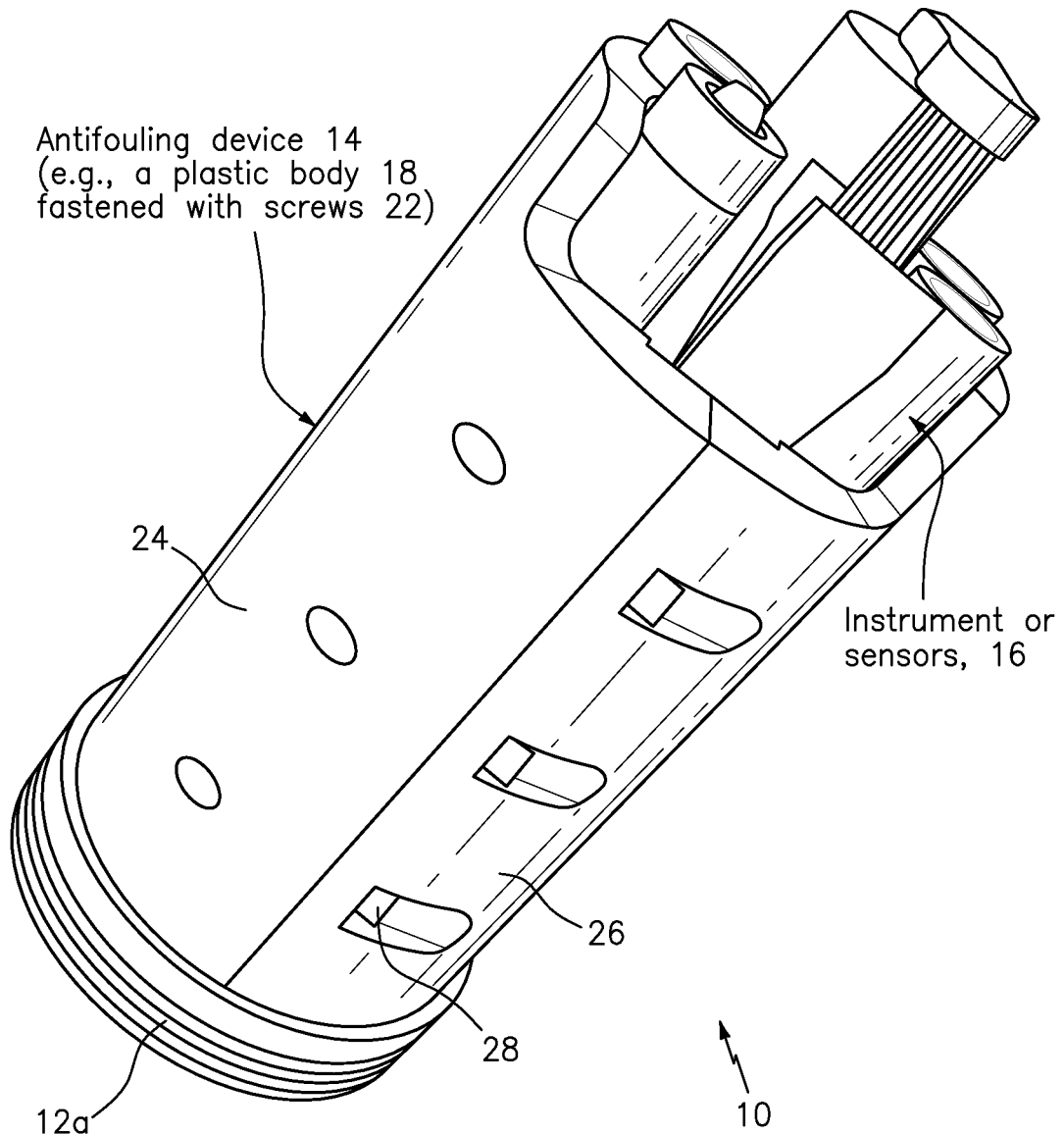
FIG. 2 is a photograph showing a sensor device having an antifouling device or guard coupled to a sensor body, where the antifouling device or guard takes the form of a plastic body having two halves coupled together with screws, according to some embodiments of the present invention.

FIG. 2 shows the sensor device 10 having the antifouling device or guard 14 coupled to the sensor body 12. In FIG. 2, two halves of the antifouling device or guard 14 are labeled 24, 26 and coupled together with the screws, one of which is labeled 28.

FIG. 3

Figure 3:
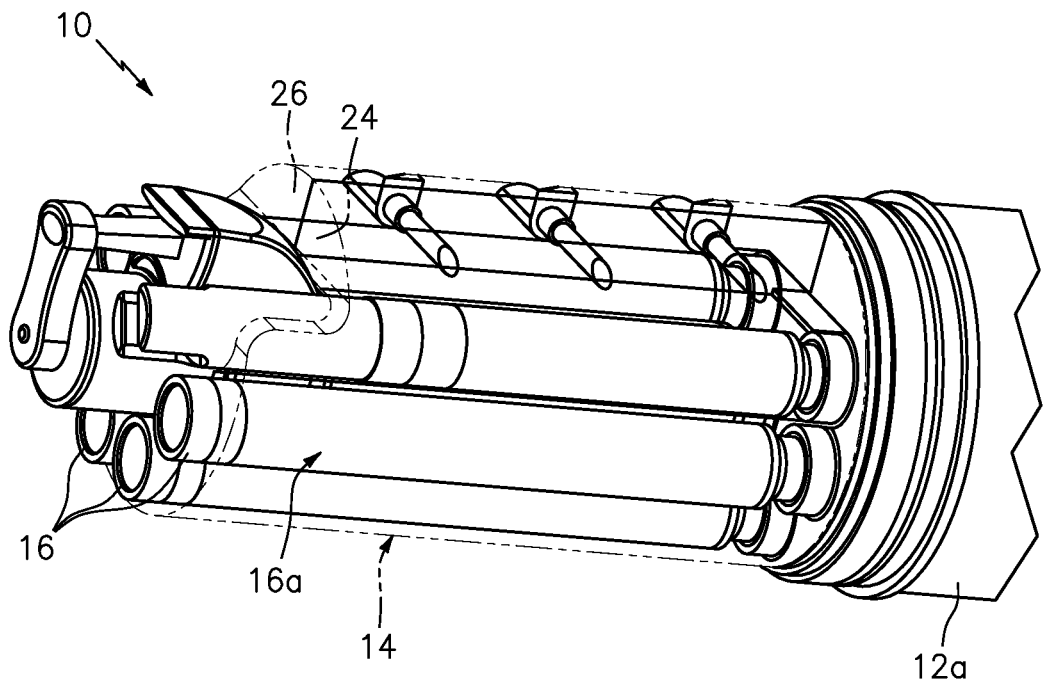
FIG. 3 is a computer rendition of a sensor device having an antifouling device or guard coupled to a sensor body, where the antifouling device or guard is shown in phantom surrounding the instruments or sensors of the sensor body, according to some embodiments of the present invention.

FIG. 3 shows the sensor device 10 having the antifouling device or guard 14 having the two halves 24, 26 coupled to the sensor body 12 having the instruments or sensors 16. In FIG. 3, the covered part of the sensors or instruments 16 is generally indicated by 16a, which points to the area of the sensors or instruments 16 covered and protected by the antifouling device or guard 14. In effect, the covered part 16a of the sensors or instruments 16 is the area underneath the antifouling device or guard 14.

FIG. 4

Figure 4:
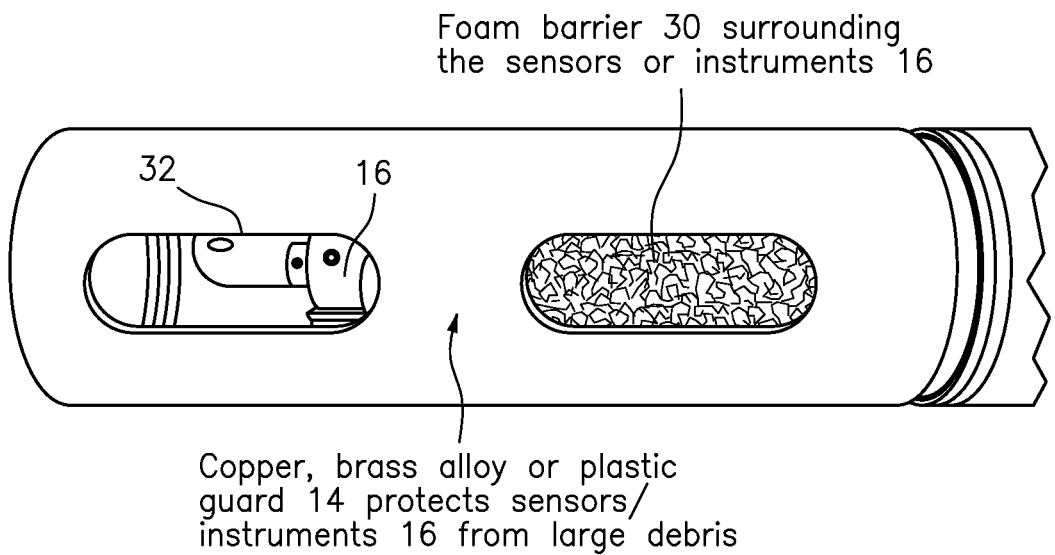
FIG. 4 is a photograph showing a sensor device having an antifouling device or guard coupled to a sensor body, where the antifouling device or guard takes the form of a copper, brass alloy or plastic guard that protects the sensors/instruments from large debris, and where the sensor device includes a foam barrier surrounding body that protects the sensors/instruments, according to some embodiments of the present invention.

By way of further example, FIG. 4 shows the sensor device 10 having the antifouling device or guard 14 coupled to the sensor body 12, The antifouling device or guard 14 may take the form of a copper, brass alloy or plastic guard configured to protect the sensors/instruments 16 from large debris, e.g., such as macroorganisms in the water. The sensor device 10 may include a foam barrier 30 surrounding the body that protects the one or more sensors/instruments 16. The antifouling device or guard 14 may include openings/orifices configured or formed therein, one of which is labeled 32.

Consistent with that set forth in relation to that shown in FIG. 3, the covered part of the sensors or instruments is the area of the sensors or instruments covered and protected by the foam barrier 30. In effect, the covered part is the area underneath the foam barrier 30.

FIG. 5

Figure 5:
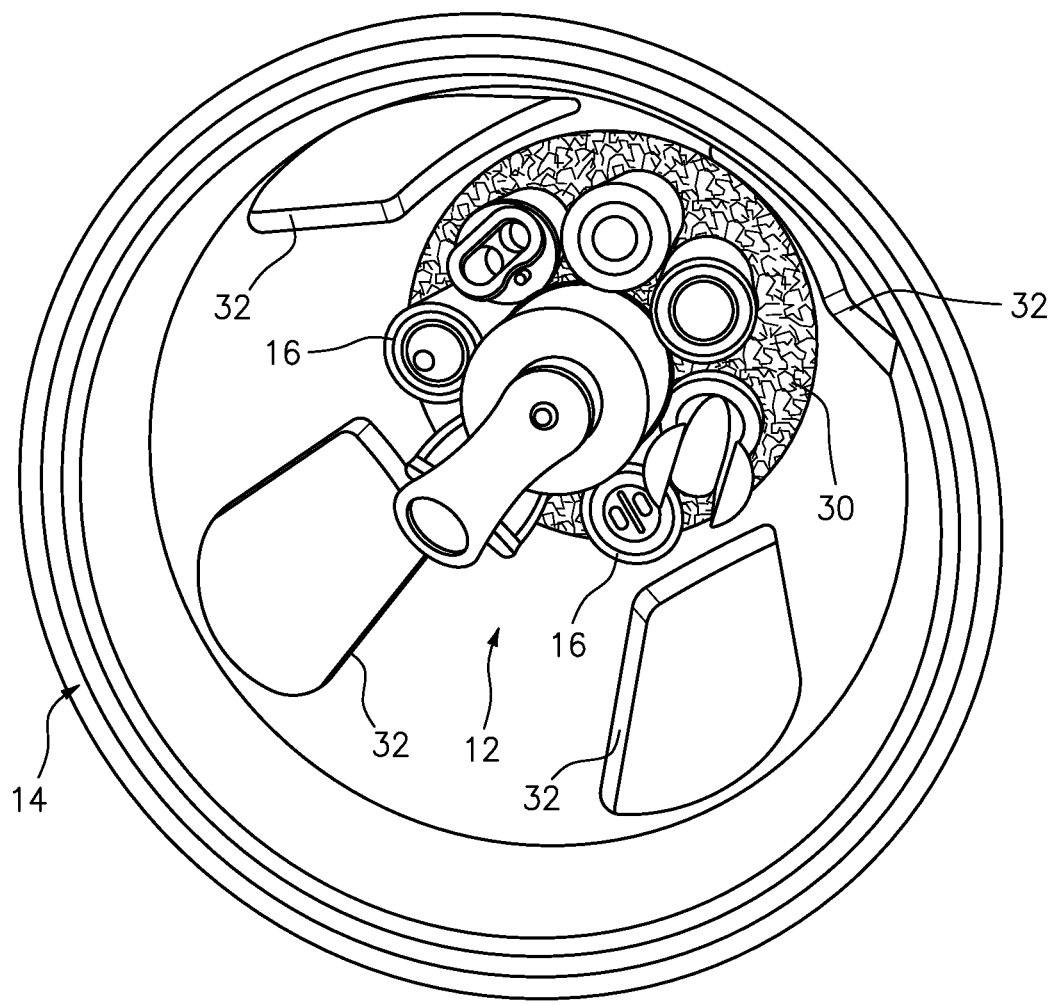
FIG. 5 is a photograph showing an inside view of a sensor device having an antifouling device or guard coupled to a sensor body, where the sensors/instruments are surrounded in foam, according to some embodiments of the present invention.

FIG. 5 shows the sensor device 10 having the antifouling device or guard 14 coupled to the sensor body 12. The sensors/instruments 16 are collectively surrounded by one piece of foam 30 configured to provide a foam barrier to protect the sensors/instruments 16 from macroorganisms.

Figure 6A:
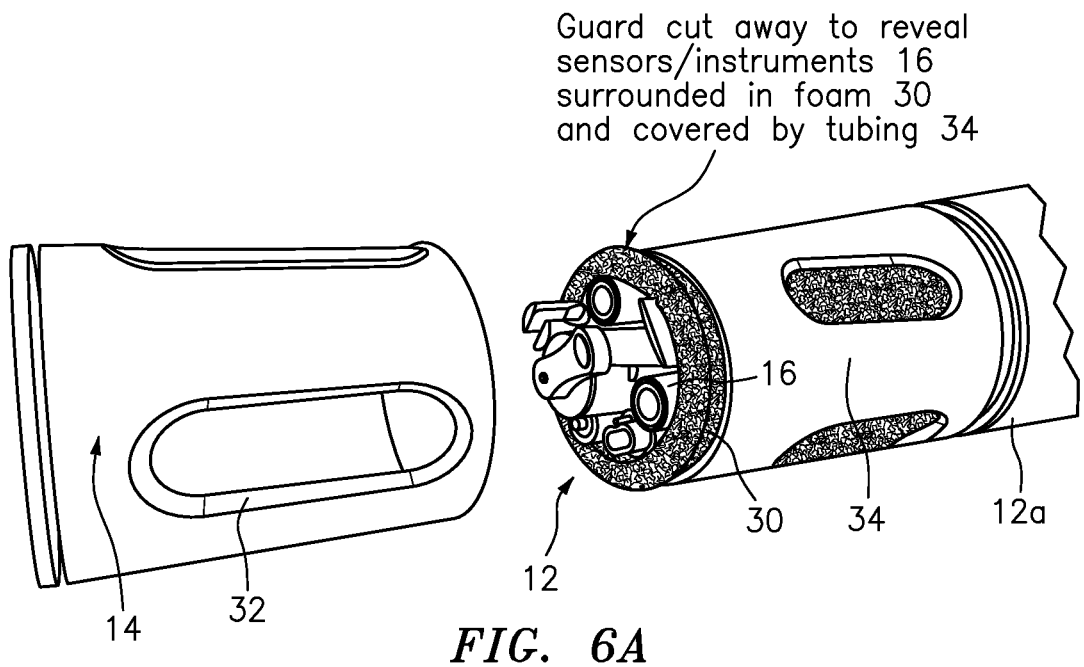
FIG. 6A is a photograph of a sensor device having an antifouling device or guard coupled to a sensor body, including showing a guard cutaway to reveal sensors/instruments surrounded in foam and covered by tubing (e.g., a heat shrink tubing), according to some embodiments of the present invention.
Figure 6B:
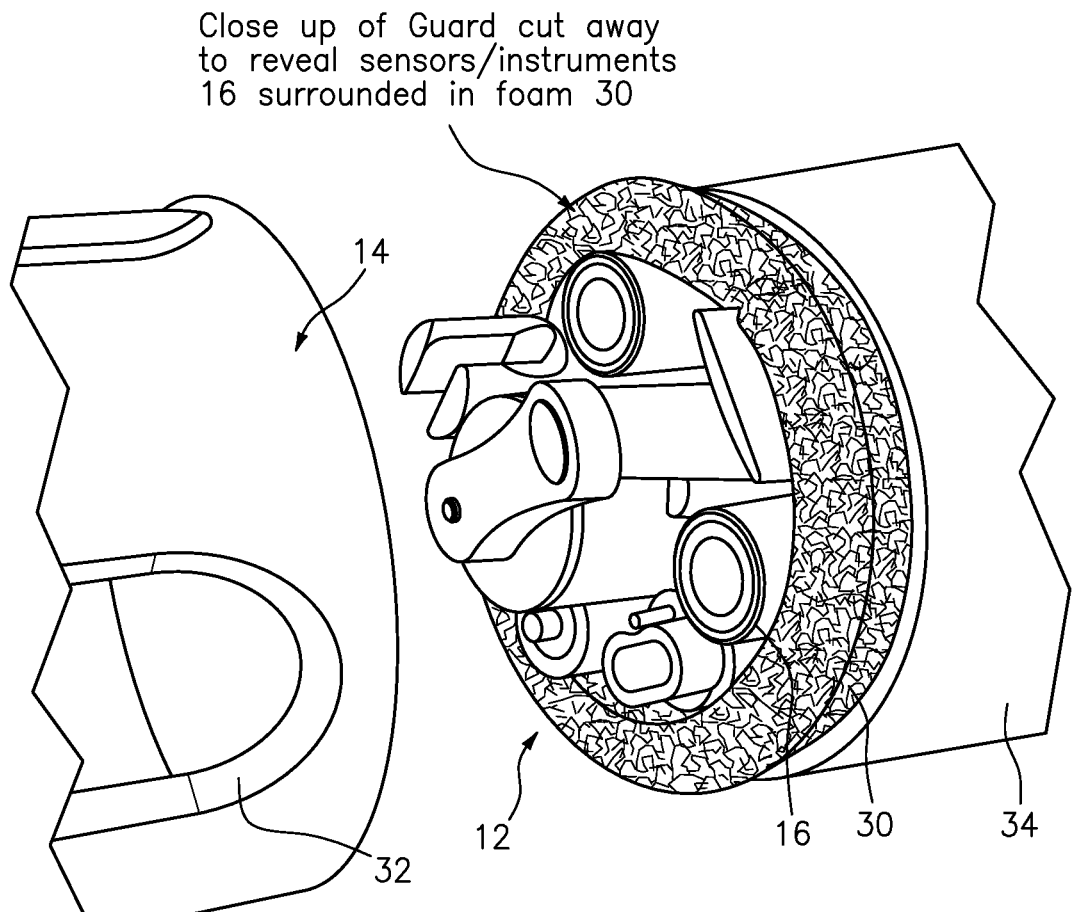
FIG. 6B is an enlarged view of part of the photograph in FIG. 6A, including the part having the guard cutaway to reveal the sensors/instruments surrounded in the foam, according to some embodiments of the present invention.

FIGS. 6A and 6B

FIGS. 6A and 6B show a sensor device 10 having the antifouling device or guard 14 coupled to the sensor body 12. e.g., including showing a guard cutaway to reveal the one or more sensors/instruments 16 surrounded in the foam barrier 30 and covered by a tubing 34. By way of example, the tubing 34 may include, or take the form of, a heat shrink tubing.

FIG. 7

Figure 7:
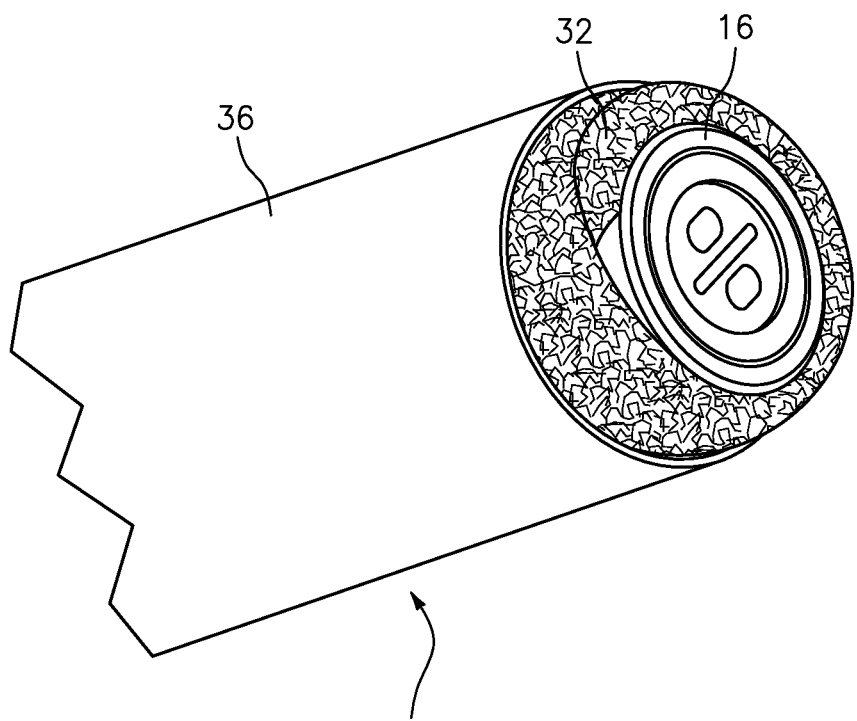
FIG. 7 is a photograph showing a single sensor/instrument individually surrounded in foam with a heat shrink tubing used to hold the foam in place, according to some embodiments of the present invention.

FIG. 7 shows a single sensor/instrument 16 surrounded or wrapped in an individual piece of foam 30, and having an individual heat shrink tubing 36 used to hold the individual pieces of foam 30 in place. In this embodiment, each individual sensor/instrument 16 may be surrounded or wrapped in a respective individual piece of foam 30. Embodiments are also envisioned, in which the individual foam wrapped sensor/instruments 16 are also collectively wrapped with a further outer foam barrier, e.g., consistent with that shown in FIGS. 4, 5 and 6A and 6B, so as to form a double foam inner/outer layer of protection.

The Instruments or Sensors 16

By way of example, the instruments or sensors 16 may be configured to sense to one or more environmental conditions in the environmental field and provide signaling containing information about the one or more environmental conditions sensed. Instruments or sensors like element 16 are known in the art, and the scope of invention is not intended to be limited to any particular type or kind either now known or later developed in the future.

Macroorganisms

As one skilled in the art would appreciate, macroorganisms are understood to be organisms that are large enough to be seen by an unaided eye. No optical instruments, such as microscopes and lens, are necessary to see them. By way of example, macroorganisms may include macrobenthos such as crustaceans and mollusks in the sea floor, barnacle, and millipedes, snails, and mites in soil.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A sensor device for deploying in a river, a stream, a lake, an estuary a sea or an ocean having large debris, including macroorganisms, comprising:
a sensor body having field sensors or instruments configured to sense parameters related to water and provide signaling containing information about the parameters sensed related to the water; and
a removable and reusable antifouling device or guard configured to install around a portion of the field instruments or sensors of the sensor body so as to form a covered part of the field instruments or sensors in an area underneath the removable and reusable antifouling device or guard for minimizing available sensor/instrument surface area for fouling from large debris, including macroorganisms, and so as to form an uncovered part of the field instruments or sensors in an associated area not underneath the removable and reusable antifouling device or guard for sensing the parameters related to the water.

2. A sensor device according to claim 1, wherein the removable and reusable antifouling device or guard comprises an antifouling body having two halves that fasten together to form the covered part and the uncovered part of the field instruments or sensors.

3. A sensor device according to claim 2, wherein the two halves are made of plastic, brass alloy, copper, plastic with an outer layer of copper, copper impregnated with plastic, plastic with a copper piece near a sensing area of the at least one instrument or sensor.

4. A sensor device according to claim 2, wherein the two halves are fastened together with screws, zip cable ties, epoxy, tape, or heat shrink wrap.

5. A sensor device according to claim 2, wherein the two halves are configured to press fit together.

6. A sensor device according to claim 1, wherein the sensor device comprises a foam barrier configured between the removable and reusable antifouling device or guard and the instruments or sensors.

7. A sensor device according to claim 6, wherein the foam barrier comprises a foam having an outer layer of copper, a copper impregnated foam, a foam with a copper piece near a sensing area of the instruments or sensors.

8. A sensor device according to claim 6, wherein the foam barrier comprises a foam that surrounds the instruments or sensors and a heat shrink tubing to hold the foam in place.

9. A sensor device according to claim 6, wherein the foam barrier comprises one piece of foam that collectively surrounds the instruments or sensors and a heat shrink tubing to hold the foam in place.

10. A sensor device according to claim 6, wherein the foam barrier comprises individual pieces of foam that respectively surrounds each of the instruments or sensors and individual heat shrink tubing to hold the individual pieces of foam in place.

11. A sensor device according to claim 2, wherein the sensor device comprises a copper insert coupled to the two halves.

12. A sensor device according to claim 11, wherein the sensor device comprises fasteners configured to fasten together the copper insert and the two halves.

13. A sensor device for deploying in a river, a stream, a lake, an estuary a sea or an ocean having large debris, including macroorganisms, comprising: a sensor body having field sensors or instruments configured to sense parameters related to water and provide signaling containing information about the parameters sensed related to the water; and a two-part removable and reusable plastic antifouling device or guard configured to install around a portion of the field instruments or sensors of the sensor body so as to form a covered part of the field instruments or sensors in an area underneath the two-part removable and reusable plastic antifouling device or guard for minimizing available sensor/instrument surface area for fouling from large debris, including macroorganisms, and so as to form an uncovered part of the field instruments or sensors in an associated area not underneath the two-part removable and reusable plastic antifouling device or guard for sensing the parameters related to the water, the two-part removable and reusable plastic antifouling device or guard having an antifouling body with two halves that fasten together with corresponding fasteners to install the two-part plastic reusable antifouling device or guard onto the sensor body and form the covered part and uncovered part of the field instruments or sensors, and that unfasten to remove the two-part removable and plastic reusable antifouling device or guard from the sensor body and clean the sensor device post deployment.

14. A sensor device according to claim 13, wherein the sensor device comprises a copper insert configured to couple to the two halves with fasteners to fasten together the copper insert and the two halves.

15. A sensor device according to claim 13, wherein the two-part removable and reusable plastic antifouling device or guard comprises two foam halves.

16. A sensor device for deploying in a river, a stream, a lake, an estuary a sea or an ocean having large debris, including macroorganisms, comprising: a sensor body having field sensors or instruments configured to sense parameters related to water and provide signaling containing information about the parameters sensed related to the water; a removable and reusable foam antifouling device or guard configured to install around a portion of the field instruments or sensors of the sensor body so as to form a covered part of the field instruments or sensors in an area underneath the removable and reusable foam antifouling device or guard for minimizing available sensor/instrument surface area for fouling from large debris, including macroorganisms, and so as to form an uncovered part of the field instruments or sensors in an associated area not underneath the removable and reusable foam antifouling device or guard for sensing the parameters related to the water; and a heat shrink tubing configured to shrink in response to heat and hold the removable and reusable foam antifouling device or guard in place.

17. A sensor device according to claim 13, wherein the removable and reusable foam antifouling device or guard is an individual piece of foam configured to wrap collectively around the field instruments or sensors.

18. A sensor device according to claim 13, wherein the removable and reusable foam antifouling device or guard comprises individual pieces of foam, each individual piece of foam being wrapped separately around a respective one of the instruments or sensors.

19. A sensor device according to claim 1, wherein the uncovered part of the field instruments or sensors in the associated area not underneath the removable and reusable antifouling device or guard is configured to contact the water for sensing the parameters related to the water.

20. A sensor device according to claim 13, wherein the uncovered part of the field instruments or sensors in the associated area not underneath the removable and reusable antifouling device or guard is configured to contact the water for sensing the parameters related to the water.

21. A sensor device according to claim 16, wherein the uncovered part of the field instruments or sensors in the associated area not underneath the removable and reusable antifouling device or guard is configured to contact the water for sensing the parameters related to the water.

* * * * *